United States Patent [19]

Ullman et al.

[11] 4,040,907
[45] Aug. 9, 1977

[54] IODOTHYRONINE ENZYME CONJUGATES

[75] Inventors: Edwin F. Ullman, Atherton; Kenneth E. Rubenstein, Menlo Park, both of Calif.

[73] Assignee: Syva Company, Palo Alto, Calif.

[21] Appl. No.: 644,489

[22] Filed: Dec. 29, 1975

Related U.S. Application Data

[60] Continuation-in-part of Ser. No. 481,023, June 20, 1974, Pat. No. 3,975,237, which is a division of Ser. No. 304,157, Nov. 6, 1972, Pat. No. 3,852,157, which is a continuation-in-part of Ser. No. 143,609, May 14, 1971, abandoned.

[51] Int. Cl.² ............................................. C07G 7/02
[52] U.S. Cl. .............................. 195/63; 195/103.5 R
[58] Field of Search .......................... 195/63, 103.5 R

[56] References Cited

U.S. PATENT DOCUMENTS

| 3,839,153 | 10/1974 | Schuurs et al. | 195/63 |
| 3,850,752 | 11/1974 | Schuurs et al. | 195/63 |

OTHER PUBLICATIONS

Medical Pharmacology, 7th Edition, pp. 490–497 (1974).

*Primary Examiner*—Alvin E. Tanenholtz
*Attorney, Agent, or Firm*—Townsend and Townsend

[57] ABSTRACT

Polyiodothyronine conjugates to enzymes are provided which find use in the determination of polyiodothyronine compounds, particularly thyroxine, normally in physiological fluids, such as serum. The enzymes can provide substantial variation in activity when bound to protein receptors for polyiodothyronine as compared to the free or unbound polyiodothyronine conjugated to the enzyme. Various linking groups are provided for linking the polyiodothyronine to the enzyme.

16 Claims, No Drawings

IODOTHYRONINE ENZYME CONJUGATES

CROSS REFERENCE TO RELATED APPLICATIONS

This application is a continuation-in-part of application Ser. No. 481,023, filed June 20, 1974, now U.S. Pat. No. 3,975,237 which in turn is a division of application Ser. No. 304,157, filed Nov. 6, 1972, now U.S. Pat. No. 3,852,157, which in turn was a continuation-in-part of application Ser. No. 143,609, filed May 14, 1971, now abandoned, the appropriate portions of which are incorporated herein, by reference.

BACKGROUND OF THE INVENTION

1. Field of the Invention

Thyroxine is an important hormone in the mammalian physiology, being excreted by the thyroid gland. The measurement of thyroxine is an important diagnostic tool in the determination of the disease. Various techniques have been used for the determination of thyroxine, including radioimmunoassay, competitive protein binding, chromatography, etc. These techniques suffer from a number of disadvantages in being difficult to carry out and in the case of radioimmunoassay having unstable reagents.

2. Description of the Prior Art

U.S. Pat. No. 3,817,837 describes enzyme immunoassays. Netherland Application Nos. 70/18838, 70/16396, 72/06373 and 71/01728 describe a number of different enzyme conjugates.

SUMMARY OF THE INVENTION

Polyiodothyronine conjugates to enzymes are provided whereby the resulting enzyme finds use in immunoassays. The enzyme conjugates are capable of competing with polyiodothyronine in a sample solution for receptor sites, particularly antibody sites. The binding of the antibody to the polyiodothyronine conjugated enzyme may provide substantial differences in enzymatic activity between antibody bound and antibody unbound enzyme conjugate. By determining in an assay sample the enzymatic activity in relation to known standards, th amount of polyiodothyronine in the sample can be determined.

The polyiodothronine is conjugated by relatively short chains to amino groups of the enzyme through a non-oxo-carbonyl linkage, including the nitrogen and sulphur analogs thereof.

DESCRIPTION OF THE SPECIFIC EMBODIMENTS

The compositions of this invention are polyiodothyronine, particularly thyroxine (3,5,3',5'-tetraiodothyronine) conjugated to an enzyme, where the enzymatic activity of the enzyme conjugate undergoes a substantial change when bound to a receptor for the polyiodothyronine. The number of thyroxines conjugated to the enzyme will be at least 1, more usually at least 2, generally not exceeding 20, more usually not exceeding 16, and preferably within the range of about 2 to 12 on the average. The enzyme conjugate will be capable of being employed in an immunoassay, so that in combination with an antibody and the unknown sample suspected of containing thyroxine, one will be able to determine the amount of thyroxine in the unknown by comparison of the enzymatic activity of the assay sample compared to known standards.

The polyiodothyronine may be linked at the carboxyl group, the amino group, or the phenolic hydroxyl and the linking group may be a simple bond, particularly in the case of the carboxyl or may be a chain having from 1 to 16, more usually from 1 to 12, and preferably from about 2 to 8 atoms in the chain other than hydrogen, which will be carbon, oxygen, nitrogen (as amido or tertiary amino), or sulphur. The oxygen and sulfur (chalcogen) will be present as oxy or thioether in the chain and normally bonded solely to carbon. The nitrogen will be bonded solely to carbon and hydrogen, being bonded to hydrogen solely when an amido nitrogen. The total number of atoms in the linking group, excluding hydrogen and the atoms provided by the enzyme and the polyiodothyronine, will generally be at least 2, not more than about 20, usually not more than about 16. The atoms in the linking group will be carbon, hydrogen, oxygen, nitrogen and sulfur, with oxygen being oxy or oxo, particularly oxo when a side group, with nitrogen and sulfur normally part of the chain or present as oxo analogs. (Oxy is hydroxyl or ether.) The functionality of the linking group joined to the polyiodothyronine will depend upon the particular site of attachment to the polyiodothyronine, and may be a bond or a non-oxo-carbonyl group (including nitrogen and sulphur analogs thereof). The same type of linking group may be employed in bonding to the available amino groups or phenolic hydroxyl groups of the enzyme.

For the most part, the polyiodothyronine conjugates will have the following formula:

$$\left( W^2O - \underset{\alpha^4}{\overset{\alpha^3}{\bigcirc}} - O - \underset{\alpha^2}{\overset{\alpha^1}{\bigcirc}} - CH_2 - \underset{(NW)_xL}{\overset{|}{C}}H - COW^1 \right)_n - A$$

wherein:

any one of the W groups can be X or an H of any one of the W groups may be replaced by X, wherein X is a bond or linking group;

A is an enzyme bonded at other than its active site having $n$ number of ligands in the range of 1 to the molecular weight of A divided by 2,000, usually in the range of 1 to 20, more usually in the range of 2 to 16, and preferably in the range of 2 to 12;

(By "active site" is intended those amino acid units or groups necessary for enzyme activity.)

$x$ is 0 or 1, being 0 when $W^1$ is the linking group;

L is hydrogen, or when $W^2$ is the linking group, lower alkyl of from 1 to 3 carbon atoms, particularly methyl, or a protective acyl group e.g. benzyloxycarbonyl, t-butoxycarbonyl, trifluoroacetyl, etc.;

$\alpha^{1-4}$ are usually iodine, although one of $\alpha^2$ and $\alpha^4$ may be hydrogen;

when other than a linking group:

W is hydrogen, with the proviso that when L is lower alkyl, W is the same or different lower alkyl of from one to three carbon atoms, particularly methyl;

$W^1$ is hydroxyl or lower alkoxyl of from one to three carbon atoms, particularly methoxy; and $W^2$ is hydrogen.

For the most part, the enzyme conjugates of this invention will have the following formula:

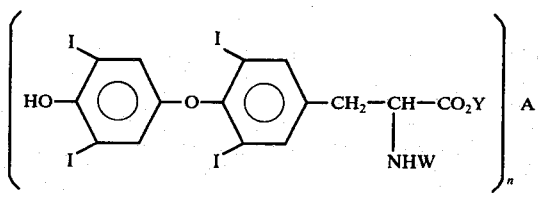

wherein:

n, A and W have been defined previously;

Y is hydrogen or lower alkyl (1 to 3 carbon atoms, particularly methyl).

For the most part, the linking group to the enzyme will either be a bond through a saturated aliphatic carbon atom or an amide linkage (including the nitrogen and thioanalogs thereof i.e. amidine and thioamide), that is, bonded to available amino groups from particularly lysine, histidine or tryptophane or terminal amino groups, or bonded to hydroxyl groups to form ethers or esters, for example, to tyrosine or serine.

Prefered groups for X will have the following formula:

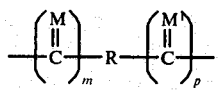

wherein:

m and p are either 0 or 1, the sum of m plus p being 0 to 2, preferably 1 to 2;

M and $M^1$ are chalcogen (O and S) and nitrogen (as amino) preferably oxygen;

R is a bond or an aliphatic group of from 1 to 12, more usually 1 to 10, and preferably from 2 to 4 atoms other than H which includes carbon and from 0 to 5 heteroatoms, preferably 0 to 3 heteroatoms the heteroatoms being chalcogen or nitrogen, the nitrogen being normally present free of attached hydrogen atoms, e.g. as tertiary amino, or as amido, the chalcogen being bonded solely to carbon and hydrogen particularly carbon: when other than a bond, R will normally have a total number of carbon atoms of from 1 to 10, more usually 1 to 8, and preferably from 2 to 6, more preferably from 2 to 4.

Illustrative R groups include methylene, dimethylene, tetramethylene, hexamethylene, N-ethyl methyleneaminomethylene, N-methyl ethyleneaminoethylene, aminoethylene, ethyleneoxyethylene, and methyleneoxyethylene.

A wide variety of enzymes may be employed. As a practical matter, there are a number of groups of enzymes which are preferred, and among these groups, there are particular enzymes which are preferred. Employing the International Union of Biochemical (I.U.B.) Classification, the oxidoreductases (1.), the hydrolases (3.), and isomerases are preferred classes.

"1. Oxidoreductases
  1.1 Acting on the CH-OH group of donors
    1.1.1 With NAD or NADP as acceptor
      1. alcohol dehydrogenase
      6. glycerol dehydrogenase
      26. glyoxylate reductase
      27. L-lactate dehydrogenase
      37. malate dehydrogenase
      49. glucose 6-phosphate dehydrogenase
      17. mannitol 1-phosphate dehydrogenase -continued 1.1.2 With cytochrome as an acceptor
      3. L-lactate dehydrogenase
    1.1.3 With $O_2$ as acceptor
      4. glucose oxidase
      9. galactose oxidase
  1.2 Acting on the CH-$NH_2$ group of donors
    1.4.3 With $O_2$ as acceptor
      2. L-amino acid oxidase
      3. D-amino acid oxidase
  1.6 Acting on reduced NAD or NADP as donor
    1.6.99 With other acceptors
      diaphorase
  1.10 Acting on diphenols and related substances as donors
    1.10.3 With $O_2$ as acceptor
      1. polyphenol oxidase
      3. ascorbate oxidase
  1.11 Acting on $H_2O_2$ as acceptor
    1.11.1
      6. catalase
      7. peroxidase"

Of the various enzymes, the following table indicates enzymes of particular interest set forth in accordance with the I.U.B. classification.

1. Oxidoreductases
  1.1 Acting on the CH-OH group of donors
    1.1.1 With NAD or NADP as acceptor
      1. alcohol dehydrogenase
      6. glycerol dehydrogenase
      26. glyoxylate reductase
      27. L-lactate dehydrogenase
      37. malate dehydrogenase
      49. glucose 6-phosphate dehydrogenase
      17. mannitol 1-phosphate dehydrogenase
    1.1.2 With cytochrome as an acceptor
      3. L-lactate dehydrogenase
    1.1.3 With $O_2$ as acceptor
      4. glucose oxidase
      9. galactose oxidase
  1.2 Acting on the CH-$NH_2$ group of donors
    1.4.3 With $O_2$ as acceptor
      2. L-amino acid oxidase
      3. D-amino acid oxidase
  1.6 Acting on reduced NAD or NADP as donor
    1.6.99 With other acceptors
      Diaphorase
  1.10 Acting on diphenols and related substances as donors
    1.10.3 With $O_2$ as acceptor
      1. polyphenol oxidase
      3. ascorbate oxidase
  1.11 Acting on $H_2O_2$ as acceptor
    1.11.1
      6. catalase
      7. peroxidase
3. Hydrolases
  3.1 Acting on ester bonds
    3.1.1 Carboxylic ester hydrolases
      7. cholinesterase
    3.1.3 Phosphoric monoester hydrolases
      1. alkaline phosphatase
    3.1.4 Phosphoric diester hydrolases
      3. phospholipase C
  3.2 Acting on glycosyl compounds
    3.2.1 Glycoside hydrolases
      1. α-amylase
      4. cellulase
      17. lysozyme
      23. β-galactosidase
      27. amyloglucosidase
      31. β-glucuronidase
  3.4 Acting on peptide bonds
    3.4.2 Peptidyl-amino acid hydrolase
      1. carboxypeptidase A
    3.4.4 Peptidyl-peptide hydrolase
      5. α-chymotrypsin
      10. papain
  3.5 Acting on C-N bonds other than peptide bonds
    3.5.1 In linear amides
      5. urease
  3.6 Acting on acid anhydride bonds
    3.6.1 In phosphoryl-containing anhydrides
      1. inorganic pyrophosphatase
4. Lyases
  4.1 Carbon-carbon lyases
    4.1.2 Aldehyde lyases
      7. aldolase
  4.2 Carbon-oxygen lyases
    4.2.1 Hydrolases -continued

|   |   |   |   | 1. carbonic anhydrase |
|---|---|---|---|---|
| 4.3 | Carbon-nitrogen lyases | | | |
| | 4.3.1 | Ammonia lyases | | |
| | | 3. histidase | | |
| 5. | Isomerases | | | |
| | 5.1 | Racemases and epimerases | | |
| | | 5.1.3 | Acting on carbohydrates and derivatives | |
| | | | Triose phosphate isomerase | |

From the standpoint of operability, a very wide variety of enzymes can be used. But, as a practical matter, there will be a number of groups of enzymes which are preferred. Employing the International Union of Biochemical (I.U.B.) Classification, the oxidoreductases (1.) and the hydrolases (3.) will be of greatest interest, while the lyases (4.) will be of lesser interest.

Of the oxidoreductases, the ones acting on the CHOH group, the aldehyde or keto group, or the CH-NH$_2$ group as donors (1.1, 1.2, and 1.4 respectively) and those acting on hydrogen peroxide as acceptor (1.11) will be preferred. Also, among the oxidoreductases as preferable will be those which employ nicotinamide adenine dinucleotide, or its phosphate or cytochrome as an acceptor, namely 1.X.1 and 1.X.2 respectively, under the I.U.B. Classification.

Of the hydrolases, of particular interest are those acting on glycosyl compounds, particularly glycoside hydrolases, and those acting on ester bonds, both organic and inorganic esters, namely the 3.1 and 3.2 groups respectively, under the I.U.B. Classification.

Other groups of enzymes which might find use are the transferases, the lyases, the isomerases, and the ligases.

Preferably, the enzyme which is employed or other enzymes, with like activity, will not be present in the fluid to be measured, or can be easily removed or deactivated prior to the addition of the assay reagents. Also one would want that there not be naturally occurring inhibitors for the enzyme present in fluids to be assayed.

Also, although enzymes of up to 600,000 molecular weight can be employed, usually relatively low molecular weight enzymes will be employed of from 10,000 to 300,000 molecular weight, more usually from about 10,000 to 150,000 molecular weight, and frequently from 10,000 to 100,000 molecular weight. Where an enzyme has a plurality of subunits the molecular weight limitations refer to the enzyme and not to the subunits.

For synthetic convenience, it is preferable that there be a reasonable number of groups to which the ligand may be bonded, particularly amino groups. However, other groups to which the ligand may be bonded include hydroxyl groups, thiols, and activated aromatic rings, e.g., phenolic, imidazoles and indoles.

ENZYME ASSAY

The polyiodothyronine enzyme conjugates can be used in a wide variety of immunoassays, either employing a separation step or not employing a separation step, the latter being referred to as homogeneous enzyme immunoassays. These types of assays have been extensively described in the literature which has been referred to previously. It is found that with polyiodothyronines, particularly thyroxine, and certain enzymes, rather than inhibition, when the polyiodothyronine is bound to antipolyiodothyronine, activation of the enzyme is obtained. The conjugated enzyme is highly deactivated, generally having less than 50% of the activity of the unconjugated enzyme, usually less than 30%, and more usually less than 10% of the activity of the unconjugated enzyme. Conveniently, the enzyme can have as little as 1%, even as little as 0.5% of the original enzyme activity.

Upon combining the conjugated enzyme with excess antibody, an amount sufficient to combine with all of the available polyiodothyronines, an increase in activity of at least 30%, usually at least 100%, and preferably at least 200% of the enzyme activity of the conjugated enzyme is obtained. Generally, the antibody bound conjugated enzyme will not have more than 60% of the original activity of the unconjugated enzyme.

Thus, depending upon the enzyme, the assay can be run in three different ways. For illustrative purposes, thyroxine will be referred to.

In the heterogeneous manner, the enzyme conjugate, sample, and thyroxine receptor, usually antibody or thyroglobulin, are combined in a suitable buffered medium, the mixture incubated for a sufficient time, and the enzyme conjugated bound to receptor separated from the unbound enzyme conjugate by any convenient means. Most conveniently, antibodies to the receptors are employed which aid in a clean separation of the receptor from the assay medium. The assay medium may then be assayed for remaining enzyme conjugate. In this situation, it is desirable to have minimum deactivation of the enzyme conjugate and more than one thyroxine conjugated to the enzyme is not necessary.

In the homogeneous manner, the method is the same whether the enzyme is activated or deactivated by binding to the receptor. Thus, one again combines the enzyme conjugate, receptor and sample, incubates for a sufficient time, and then determines the enzyme activity in the solution without separation.

In all instances, the amount of thyroxine in the sample is determined by comparing the results of the assay to known standards. That is, samples having known amounts of thyroxine are prepared and the assay carried out and the enzymatic activity determined. The enzymatic activity is then graphed against the thyroxine concentration and the graph used to determine the amount of thyroxine in an unknown.

The conditions for the assay will vary depending upon the particular enzyme and method employed. Where the homogeneous technique is used, the conditions will be selected so as to optimize the change in activity of the enzyme conjugate upon binding by the receptor. Normally, the pH will be in the range of about 5.5 to 10, more usually in the range of about 7 to 9.5, where strong binding between receptor and thyroxine occurs. Moderate temperatures will be employed, normally in the range of about 0° to 45°, more usually about 20° to 40° C.

The buffer solution employed will normally be at a concentration to provide in the assay medium, a concentration of from about 0.001 to 0.5M, usually from about 0.01 to 0.2M. Protein will frequently be included to stabilize the enzyme; the protein can be an albumin, such as rabbit serum albumin, and/or gelatin, and will generally be present in about 0.005 to 0.5 weight percent in the final assay mixture, more usually from about 0.01 to 0.2 weight percent. Other additives may be present as is found desirable, such as glycerol, Thimerosal, sodium azide, etc.

concentration of the enzyme conjugate will vary widely, depending on the particular enzyme, the concentration of throxine of interest, and the like. Normally, the enzyme concentration will be from about $10^{-5}$ to $10^{-12}$ M, more usually from about $10^{-7}$ to $10^{-11}$M. The ratio of binding sites to the concentration of conjugated polyiodothyronine will generally be at least about 0.5 and not greater than 1000, more usually being about from 1 to 100.

The order of addition of the reagents is not critical. However, it is preferred that the enzyme conjugate and receptor not be combined prior to the addition of the sample. The preferred order of addition is the sample and antibody, followed by the addition of enzyme conjugate. The particular substrates for the enzyme may be added as convenient. After each step the assay mixture may be incubated. Usually, incubation periods will be from about 10 seconds to 1 hour.

Enzyme activity determinations can be carried out for a duration of from about 5 seconds to 60 minutes, more usually being from about 0.5 to 30 minutes.

For the most part, spectrophotometric techniques will be employed. However, other techniques include fluorimetry, titrimetric, etc.

The following examples are offered by way of illustration and not by way of limitation.

EXPERIMENTAL (All temperatures not otherwise indicated are in Centigrade. All percents not otherwise indicated are by weight.)

EXAMPLE I

N-Methyl, N-carboxymethylglycyl Thyroxine Methyl Ester ($T_4$-MEMIDA)

Into a 25ml flask equipped with stirrer and septum stopper was charged 1.054g ($1.27 \times 10^{-3}$mole) of the methyl ester of thyroxine hydrochloride. The thyroxine ester hydrochloride was dissolved under an argon blanked in 8ml of dimethyl formamide (DMF) to which was added 10ml of dry tetrahydrofuran (THF), followed by the addition of 253µl of dry triethylamine.

After stirring the mixture for 15 minutes, 0.279g ($2.16 \times 10^{-3}$mole) of N-methyl iminodiacetic acid anhydride in 2.5ml of dry THF was added in one addition. The reaction appeared to occur instantaneously. Volatiles were removed in vacuo on a rotary evaporator to leave a foamy solid which was dissolved in 25ml THF and the THF solution extracted with a combination of 30ml of deionized water and 50ml of ethyl acetate. After extraction and separation, the aqueous layer was extracted three times with 25ml portions of ethyl acetate. The organic layers were then combined, extracted once with 50ml of saturated NaCl solution and then dried with anhydrous magnesium sulfate. After suction filtration of the organic layer, the solvent was removed on a rotary evaporator to yield a white solid which was dissolved in 30ml of THF. To the THF was added 35ml of chloroform, the solution heated to reflux, and n-heptane added slowly. The volume of the solution was reduced until a definite cloud persisted. The solution was allowed to cool at room temperature, followed by cooling in a freezer, to yield a white fluffy product, which was washed with n-hexane, and dried in vacuo over phosphorus pentoxide to yield 1.26g (75%) of a fluffy white product.

EXAMPLE II

Conjugation of $T_4$-MEMIDA to Bovine Serum Albumin (BSA)

To a reaction vessel equipped with stirrer and septumed glass stopper was charged 0.10g ($1.09 \times 10^{-4}$mole) of $T_4$-MEMIDA and 0.013g ($1.1 \times 10^{-4}$mole) of N-hydroxy succinimide. To the reaction vessel under an argon blanket was added one ml of dry THF followed by the addition of 15µl of dry triethylamine. After cooling the mixture in an ice bath to 0°, 0.024g ($1.25 \times 10^{-4}$mole) of 1-ethyl-3-(3'-dimethylaminopropyl) carbodiimide hydrochloride (ECDI) was added as a powder. The mixture was stirred for 2 hours at 0° followed by 12 hours at 4°. A solution was prepared of 0.100g ($1.55 \times 10^{-6}$mole) of BSA in 3.0ml of sodium bicarbonate-carbonate buffer, pH 9.4, and the pH readjusted to 9.5 with 6N sodium hydroxide. The BSA solution was cooled to 0°, and the above prepared ester solution added dropwise at a rate of 50µ/min. with vigorous stirring. The initially turbid and now clear mixture was stirred at 0° for 80 min., followed by stirring gently for 2 days at 4°.

To the solution was then added dropwise a 3M hydroxylamine hydrochloride solution neutralized to pH 8.9 with 6N sodium hydroxide. After stirring the mixture for 10 hours at 4°, the mixture was placed in a dialysis bag and dialyzed against two 500ml portions of Tris-HCl buffer (0.05M, pH 7.8) for one day. The volume of the protein mixture was then concentrated to 25ml with Aquacide II (available from Calbiochem) and twice subjected to gel filtration chromatography, using each time, freshly packed Sephadex G-15, initially swollen in Tris-HCl buffer, 0.1M, pH 9.0. The column size was $2.6 \times 22.2$cm, the flow rate was 48 drops per minute, 40 drop fractions were collected, and the buffer of elution was Tris-HCl, 0.1M, pH 9.0. The protein fractions were pooled and dialyzed against deionized water ($5 \times 2,000$ml portions) for 3 days. The conjugate solution was then lyophilized to yield 0.151g of a white fluffy solid which was dried in vacuo over $P_2O_5$ for 3 days to yield 0.140g of conjugate. Ultraviolet analysis indicated that 22 haptens were bound to each molecule of BSA.

EXAMPLE III $T_4$-MEMIDA Conjugate to Malate Dehydrogenase

Into 250µl of dry DMF was dissolved 10mg (11µmole) of $T_4$-MEMIDA and 1.3mg of N-hydroxy succinimide (NHS). The reaction mixture was kept at 0° under a nitrogen blanket with stirring and 2.3mg ECDI was added and the mixture maintained at 0° until the ECDI had dissolved. The solution was allowed to stand at 4° overnight.

A generalized procedure for preparing the conjugate is provided, with greater or lesser hapten numbers, depending upon the amount of the $T_4$-MEMIDA N-hydroxy succinimide ester employed in relation to the MDH. To 4ml of a stirring solution of m-MDH (pig heart, mitachondrial, Miles, 5.0mg/ml) in carbonate buffer, pH 9.2, was added one ml DMF. Successive additions of the $T_4$-MEMIDA ester solution were then made at about 60 to 90 minute invervals and aliquots withdrawn and assayed for enzyme activity. The following table indicates the order of addition, the amount of the addition, the time of the addition, the ratio of added $T_4$ to MDH, and the percent deactivation observed. For activity determinations, 2 to 20µl of the conjugation mixture was added to 0.5ml 1M potassium monoacid phosphate at 0°. A 2 to 20µl aliquot of the diluted conjugate was diluted to 0.8ml with 0.1 percent rabbit serum albumin in glycine buffer, 0.1M, pH 9.5, to which was added 100µl of 0.108M NAD and 100µl of 2M, pH 9.5, sodium malate. The rates were measured between 60 and 120 seconds after introduction at 30° in a Gilford Model 300N spectrophotometer.

TABLE I

| Time | Addition T$_4$-ester µl | Total[1] Volume µl | T$_4$/MDH | T$_4$[2] Conj. | % Deactivation |
|---|---|---|---|---|---|
| | | 4996 | 0/1 | | 0 |
| 10:34 | 13 | 5007 | 2/1 | | |
| 11:24 | | 5003 | 2/1 | | 30.1 |
| | 1 ml withdrawn as conjugate c | | | 1.3 | |
| 11:30 | 10.5 | 4011 | 4/1 | | |
| 12:03 | | 4009 | 4/1 | | 85.7 |
| | 1 ml withdrawn as conjugate d | | | 2.8 | |
| 1:10 | 8 | 3001 | 6/1 | | |
| 1:37 | | 2991 | 6/1 | | 94.0 |
| | 1 ml withdrawn as conjugate e | | | 3.7 | |
| 1:58 | 5.5 | 1977 | 8.1/1 | | |
| 2:49 | 4 | 1941 | 9.6/1 | | 98.8 |
| | 1 ml withdrawn as conjugate f | | | 5.6 | |

[1]samples were periodically withdrawn and the enzme activity determined which were not reported, which affect the total volume reported
[2]No. of T$_4$'s bound to MDH

EXAMPLE IV

T$_4$-MEMIDA Conjugate to Triose Phosphate Isomerase (TIM)

Into 500µl of dry DMF in a vial was introduced 6.0mg (6.8µmoles) T$_4$-MEMIDA and 0.8mg (7.3µmoles)-N-hydroxy succinimide, the vial flushed with dry argon and covered, and the mixture cooled in an ice bath. To the stirred mixture was then added 1.5mg ECDI, the vial flushed with dry argon and stirred until everything dissolved. The vial was wiped dry, placed in covered plastic cup with Drierite, wrapped in foil and allowed to stand overnight at 4° with stirring.

To 1ml triose phosphate isomerase (2mg) in aqueous carbonate buffer (0.1M, pH 9.2) at 4° 0.3ml DMF was added slowly with syringe. The ester solution was added slowly in increments by syringe and the enzyme activity monotored. When the enzyme was approximately 72% deactivated, DMF was added to bring the solution to 40% volume DMF.

The cold reaction mixture was passed through a Sephadex G-25-(medium) column equilibrated with 0.1m carbonate buffer, pH 9.2. The column was a 50cc buret, 1.1cm in diameter with a bed volume of ~19ml. The elution was carried out at 4° with a solution of 60 parts by volume of an aqueous solution 0.1M CO$_3$, pH 9.2 and 0.3M ammonium sulfate and 40 parts of DMF. Fractions were collected varying in volume from about 1 to 4ml. Fractions 5 and 6 were pooled (2.4ml) and dialyzed first against ~100ml aqueous 20 volume % DMF, 0.02M triethanolamine (TEA), pH 7.9, then 3×250ml aqueous 0.02 TEA, pH 7.9. The ratio of conjugated T-4 to enzyme was about 6.

EXAMPLE V

T$_4$-MEMIDA Conjugate to Glucose Oxidase

The T$_4$-MEMIDA N-hydroxy succinimide (NHS) ester was prepared as described in Example IV, using 9.9mg T$_4$-MEMIDA, 1.5mg NHS and 2.4mg ECDI in 500µDMF.

To 0.4ml (4mg) glucose oxidase Type 5 (A. niger, Sigma) stock solution was added 0.1ml 0.25M CO$_3$, pH 9.2 at 4° with stirring. To the stirred mixture was slowly added 414µl DMF, followed by 86µl of the above ester solution added incrementally over 10 minutes. The reaction was allowed to continue for approximately 22 hours at 4°.

The reaction mixture was then chromatographed on a Sephadex G-50 (medium) column, bed height ~28.5cm, equilibrated with 0.1M aqueous PO$_4$ buffer, pH 6 at room temperature, eluting with 0.1M aqueous PO$_4$ buffer, pH 6, at 20 drops per fraction, ~15 fractions per hour. Fractions 5 to 10 were collected and pooled. The ratio of conjugated T-4 to enzyme (hapten number) was found by UV to be about 7.

EXAMPLE VI

DGMA Conjugate to Glucose-6-Phosphate Dehydrogenase (G-6-PDH)

To 10mg (11µmole) T$_4$-methyl ester diglycolate (See Example VIII) in 0.52ml dry DMF at 0° was added 1.3mg (11µmole) NHS and 2.3mg (12.1µmole) ECDI. The flask was flushed with nitrogen and allowed to stand over night at 4°. To 2.0mg G-6-PDH (L. mesenteroides, 0.019µmole) in 0.33ml 1mg/ml sodium bicarbonate (0.33mg, 3.8µmole) at 0° was added 1mg (3.8µmole) G-6-P and 2.5mg (3.8µmole) NADH, followed by 0.067ml DMF, followed by 1.9µmole of the above ester in 0.043ml DMF. The enzyme activity was monitored and after 2 hours, a 65% loss in activity was observed. The conjugate was purified by chromatogrphy over 3 Sephadex G-15 and G-50 columns and was found to have a hapten number of 11 by UV and 10.8 by iodine anaylsis.

Following the procedure described above, 10mg of the T$_4$ methyl ester diglycolate in 0.52ml dry DMF was reacted with 1.3mg NHS and 2.3mg ECDI. To 8.7mg G-6-PDH (0.08µ mole) in 1.65ml 1mg/ml sodium bicarbonate was added 5mg G-6-P and 12.5mg NADH, followed by 0.335ml DMF, followed by 9.5µmole ester prepared above in 0.215ml DMF. In 4 hours, a 47% loss in activity was observed. The hapten number was found to be 12 by UV and 13.2 by iodine analysis.

EXAMPLE VII

T$_4$-DGMA Conjugate to Lysozyme

To 90.7mg of the T$_4$ methyl ester diglycolate in 5ml dry DMF cooled in an ice bath was added 11.5mg NHS followed by 19.2mg ECDI and the mixture allowed to sit in the cold room (4°) over night. To 14mg of lysozyme dissolved in 2.4ml of water and 2.1ml DMF cooled in a cold room was added 0.6ml of the DMF solution prepared above diluted with 0.6ml water. After 5.5 hours of stirring in the cold room, the mixture was dialyzed against 0.025M tris/maleate, pH 6.0. After 13 hours, the dialysate was changed with some precipitate forming during the dialysis.

EXAMPLE VIII

Carboxymethoxyacetyl Thyroxine Methyl Ester (DGMA)

To a solution of 1.65g of the methyl ester of thyroxine hydrochloride in 80ml of dry THF and 30ml of chloroform in a flask protected from light was injected 300µl of triethylamine while the mixture was agitated. Diglycolic anhydride (255mg, 0.002 mole) was then added and the mixture stirred overnight. The solution was then washed 3 times with water, dried over sodium sulphate and the volatiles removed in vacuo. The residue was purified on a 30g Sephadex LH-20 column, using a solution of 20% methanol in dichloromethane as eluent. The clear fractions were collected, the solvent removed and the residue precipitated from methanol with water, yielding 1.53g, 84 percent.

EXAMPLE IX

T$_4$-MEMIDA Glycine

A 3ml Pierce Reacti-Vial was charged with 0.201g (2.18 × 10$^{-4}$mole) of T$_4$-MEMIDA and 0.025g (2.17 × 10$^{-4}$mole) of N-hydroxysuccinimide (NHS). 2.0ml of dry THF and 30μl (2.15 × 10$^{-4}$mole) of dry triethylamine was added and the reaction mixture was cooled to 0° with an ice bath. ECDI (0.048g, 2.50 × 10$^{-4}$mole) was added as a powder and the reaction mixture stirred for 35 minutes at 0°. The reaction mixture was then placed in the cold room (2°) and stirred for 15 hours. A TLC of the reaction mixture after 15 hours showed two spots with R$_f$ values of 0.06 (T$_4$-MEMIDA and 0.60 (T$_4$-MEMIDA NHS ester), on an analytical silica gel plate, with 10% methanol in dichloromethane as the irrigant. A 25ml flask, equipped with stirring flea and septum stopper, was charged with 0.033g (4.39 × 10$^{-4}$mole) of glycine, followed by 1.50ml of distilled H$_2$O, 0.50ml of pyridine, and 100μl (1.00 × 10$^{-4}$mole) of 1.0N NaOH. The reaction mixture was cooled to 0° with an ice bath. With vigorous stirring, the T$_4$-MEMIDA NHS ester solution, prepared above, was added dropwise, and after addition the reaction mixture was placed in the cold room (2°) and stirred for 36 hours. The solvents were then stripped with a rotary evaporator to yield an oily pyridine-smelling solid. This solid was taken up in 10ml MeOH and poured into 15ml H$_2$O and the solution was extracted with ethyl acetate (2 × 25ml). The combined organic layers were, extracted once with 25ml of saturated brine, then dried over anhydrous MgSO$_4$. After filtration, the ethyl acetate was stripped on a rotary evaporator to yield a white crystalline solid. The solid was taken up in 2ml of methanol and put onto four preparative silica gel plates TLC plates, which were developed in triethylamine: methanol: dichloromethane (2.1: 10:90). The plates were run twice, then were scraped and the product deabsorbed with methanol: dichloromethane (1:1). The silica gel was filtered off and the filtrate reduced to 2ml in vacuo. A TLC of the product in THF showed only one spot with a R$_f$ value of 0.50, on an analytical silica gel TLC plate, in triethylamine: methanol: dichloromethane (2.1:10:90). The product was recrystallized from THF/chloroform/cyclohexane.

EXAMPLE X

T$_4$-MEMIDA Glyclglycine

A 3ml Pierce Reacti-Vial was charged with 0.202g (2.20 × 10$^{-4}$mole) of T$_4$-MEMIDA, and 0.025g (2.17 × 10$^{-4}$mole) of NHS. Dry THF (2ml) and 31μl of dry triethylamine were added, and the reaction mixture was cooled to 0°. ECDI (0.051g, 2.66 × 10$^{-4}$mole) was added and the reaction mixture stirred in the cold room (2°) for 8.25 hours. A TLC indicated the formation of the T$_4$-MEMIDA glycylglycine NHS ester; R$_f$ value of 0.63, on an analytical silica gel plate, with triethylamine: methanol: dichloromethane (2.1:10:90). A 25ml flask, equipped with stirring flea and septum stopper, was charged with 0.058g (4.39 × 10$^{-4}$mole) of glycylglycine, followed by 1.50ml of H$_2$O and 0.50ml of pyridine and 100μl (1.0 × 10$^{-4}$mole) of 1.0N NaOH. The reaction mixture was cooled to 0°, and the T$_4$-MEMIDA NHS ester solution added dropwise with stirring. After addition of the activated ester, 1.0ml deionized H$_2$O and 0.50ml of pyridine was added. The reaction mixture was stirred in the cold room (2°) for 93 hours, worked up identical to that of T$_4$-MEMIDA glycine to yield 0.018g (9% yield) of a tan gold solid. The product was homogeneous by TLC on silica gel with triethylamine: methanol: dichloromethane (2.1:10:80); R$_f$ value of 0.81, where the plate was developed twice.

EXAMPLE XI

T$_4$-MEMIDA Glycine/m-MDH Conjugate

A 1ml Pierce Reacti-Vial, equipped with stirring flea, was charged with 0.049g (5.0 × 10$^{-6}$mole) of T$_4$-MEMIDA and 39μl of dry DMF. The reaction mixture was cooled to 0° and 10μl (5.2 × 10$^{-6}$mole) of a 5.0 × 10$^{-1}$M NHS in DMF at 0° solution and 51μl (6.1 × 10$^{-6}$mole) of a 1.2 × 10$^{-1}$M ECDI in DMF solution at 0° were added and the reaction mixture stirred in the cold room (2°) for 49 hours. A TLC of the reaction mixture, after 49 hours, showed two spots with R$_f$ values of 0.49 (T$_4$-MEMIDA glycine) and of 0.68 (T$_4$-MEMIDA glycine NHS ester), on analytical silica gel plates, developed in triethylamine: methanol: dichloromethane (2.1:10:90). m-MDH (4.0ml, 1.3 × 10$^{-5}$M, 0.05M NaHCO$_3$-Na$_2$CO$_3$, pH 9.2), was put into a 10ml round bottomed flask equipped with stirring bar and septum stopper, cooled to 0°, and the enzyme activity was determined, as described previously. Dry DMF (445μl) was added to the reaction mixture at a rate of 15μl per minute to yield a 10% DMF reaction mixture. The enzyme activity was again determined. The 4.3 × 10$^{-2}$M T$_4$-MEMIDA glycine NHS ester solution was added to the reaction mixture in 1 to 2μl aliquots, and the enzyme activity was determined after each addition. Nine microliters of the above activated ester solution gave an 82% deactivated enzyme conjugate. After the final addition of activated ester, the enzyme reaction mixture was exhaustively dialyzed against 1.0M K$_2$HPO$_4$(with 1.0 × 10$^{-3}$M NaN$_3$), at 2°. After dialysis, the enzyme conjugate was carefully removed from the dialysis bag and was passed through two Sephadex G-50M (preswollen in 1.0M K$_2$HPO$_4$, with 1.0 × 10$^{-3}$M NaN$_3$) columns. The two column sizes were 0.9 × 54.0cm and 0.9 × 51.0cm, the flow rates were 4 to 5 drops per minute, and 20 drop fractions were collected. The protein fractions were concentrated using a collodion bag apparatus, in the cold room. The hapten number was determined to be 3.0.

EXAMPLE XII

T$_4$-MEMIDA glycylglycine/m-MDH Conjugate

ECDI (0.015g, 7.8 × 10$^{-5}$mole) was dissolved in 0.50ml of dry DMF to yield a 1.6 × 10$^{-1}$M solution. NHS (0.75g, 6.5 × 10$^{-4}$mole) was dissolved in 1.0ml of dry DMF to yield a 6.5 × 10$^{-1}$M solution. Both solutions were cooled to 0°, in an ice bath, prior to use. A 1ml Pierce Reacti-Vial, equipped with stirring flea, was charged with 2.4 × 10$^{-3}$g of T$_4$-MEMIDA glycylglycine, followed by 78μl of ice cold dry DMF, cooled in an ice bath, and then 4μl of a 6.5 × 10$^{-1}$M NHS in DMF solution at 0° and 18μl of a 1.6 × 10$^{-1}$M ECDI in DMF solution at 0° were added. The reaction mixture was placed in the cold room (2°) and stirred for 20 hours. At the end of this time, a TLC of the reaction mixture showed two spots with R$_f$ values of 0.25 (T$_4$-MEMIDA glycylglycine) and of 0.59 (T$_4$-MEMIDA glycylglycine NHS ester), on analytical silica gel plates, developed in triethylamine: methanol: dichloromethane (2.1:10:90.

m-MDH (4.0ml of a 1.5 × $10^{-5}$M, 0.05M $NaHCO_3$-$Na_2CO_3$ (pH 9.2)), was put into 10ml round bottomed flask, equipped with stirring bar and septum stopper. The reaction mixture was cooled to 0°, with an ice bath, and 440µl of dry DMF was added at a rate of 50µl per minute. The enzyme activity was determined before and after the DMF addition. The 1.9 × $10^{-2}$M $T_4$-MEMIDA glycylglycine NHS ester solution was added to the reaction mixture in 3 to 10µl aliquots and the enzyme activity was determined after each addition. The addition of 29µl of the activated ester solution gave an 82% deactivated enzyme conjugate. The reaction mixture was then exhaustively dialyzed against 1.0M $K_2HPO_4$(with 1.0 × $10^{-3}$M $NaN_3$), at 2°. After dialysis, the conjugate was passed through three Sephadex G-50M columns (preswollen in 1.0M $K_2HPO_4$ with 1.0 × $10^{-3}$M $NaN_3$) and was eluted with the same buffer. The column sizes were 0.9 × 55cm, 0.9 × 56cm, and 0.9 × 56cm, the flow rates were 4 to 5 drops per minute, and 20 drop fractions were collected. The protein fractions were concentrated using a collodion bag apparatus in the cold room. The hapten number was determined to 3.9, by the method previously described.

EXAMPLE XIII

Conjugation of Desaminothyroxine to G-6-PDH

Desaminothyroxine (2.5 × $10^{-3}$g, 3.5 × $10^{-5}$mole), 1.9 × $10^{-2}$g (1.7 × $10^{-4}$mole) of NHS, and 0.50ml of dry DMF were successively added to a 1ml reaction vessol in an ice bath followed by the addition of 8.0 × $10^{-3}$g (4.2 × $10^{-5}$mole) of ECDI under $N_2$. The reaction mixture was stirred overnight at 4°.

G-6-PDH (4.9 × $10^{-3}$g, 4.7 × $10^{-8}$mole) was dissolved in 4.0ml of ice cold aqueous 0.05M $NaHCO_3$-$Na_2CO_3$ (pH 9.0) buffer. To the ice bath cooled G-6-PDH solution was slowly added with stirring, 800µl of dry DMF, followed by 5µl of the above prepared desaminothyroxine N-hydroxysuccinimide ester solution. After stirring the mixture for 1 hour at ice bath temperature, 1.0ml of a neutralized 2.0M hydroxylamine solution was added dropwise. The conjugation mixture was then dialyzed against 0.05M Tris-HCl + 1mM $NaN_3$ (pH 7.8) (3 × 1l.) for 5 days at 4°. The enzyme conjugate was then gel filtered on two Sephadex G-75M columns to yield a desaminothyroxine/G-6-PDH conjugate which was 83% deactivated, and with a hapten number of 1.4 (by iodine analysis). The conjugate was found to be inhibitable (~5% inhibition) on treatment with various anti-$T_4$ sera.

EXAMPLE XIV

Conjugation of desaminothyroxine to m-MDH

Desaminothyroxine (9.1 × $10^{-3}$g, 1.2 × $10^{-5}$mole) 1.4 × $10^{-3}$g (1.2 × $10^{-5}$mole) of NHS, and 0.25ml of dry DMF were successively added to a 1ml reaction vessel. The reaction mixture was cooled in an ice bath and 2.5 × $10^{-3}$g (1.3 × $10^{-5}$mole) of ECDI under a $N_2$ blanket. The reaction mixture was stirred overnight at 4°.

With cooling on an ice bath, and with stirring, DMF (0.23ml) was slowly added to 1.9 × $10^{-3}$g (2.8 × $10^{-8}$mole) of m-MDH in 0.83ml of 0.05M $NaNCO_3$-$Na_2CO_3$ (pH 9.0) with stirring while cooled in an ice bath. The above ester solution (5.8µl) was then added, with stirring and the stirring continued for one hour while maintaining the temperature. The conjugation mixture was gel filtered on three 0.9 × 13cm Sephadex G-50M columns to yield a desaminothyroxine/m-MDH conjugate which was 91% deactivated and which had a hapten number of 2.5 (by iodine analysis). The conjugate enzyme activity was found to be 30% activated when treated with anti $T_4$ sera.

EXAMPLE XV

Conjugation of N-Chloroacetamido Thyroxine with Thioglycolated G-6-PDH

A. Ethoxycarbonyldithiomethane (650mg, 4.3mole) in methanol (10ml) under a nitrogen atmosphere was treated with thioglycolic acid (390mg, 4.2mmole) resulting in a vigorous reaction. After 1 hr, aqueous base was added and the mixture extracted with methylene chloride. The aqueous phase was acidified and extracted with methylene chloride, and the extracts dried, filtered, and concentrated to give pure acid (550mg, 90%), a portion of which was distilled for analysis: bp 130°/0.05mm (Kugelrohr).

B. $^{14}$C-Dithiomethylacetic acid (4.4mg, 32µmole) and N-hydroxysuccinimide (NHS) (1.9mg, 16µmole) were dissolved in dry DMF (1.00ml), cooled in an ice bath, and treated with 1-(dimethylaminopropyl)-3-ethylcarbodiimide hydrochloride (EDCI) (3.4mg, 18µmole). The mixture was sealed and stirred overnight under argon at 0°. A portion (0.90ml) of the resulting solution of the NHS ester was added slowly (1µl/10sec) with rapid stirring to G-6-PDH (16.0mg) in 10.3ml 0.055M Tris pH 8.3 containing 100mg sodium glucose-6-phosphate and 200mg of the sodium salt of NADH at 0°. After overnight stirring, the enzyme conjugate was quantitatively transferred to a dialysis sack using 2–0.5ml buffer washes and dialyzed for 6 days against 7 × 250ml portions of 0.055M Tris, 0°. Analysis of the conjugate indicated fourteen $CH_3SS^{14}CH_2CO$-residues covalently linked.

C. Prior to reduction, $^{14}$C-Dithiomethylacetylated G-6-PDH (14 $CH_3SS^{14}CH_2CO$-residues in 0.055M Tris, pH 7.9) was dialyzed into 0.05M phosphate, pH 7.5. A portion (1.00ml containing 0.95mg enzyme) was diluted with 0.25ml carbitol slowly (1µl/3 sec) at 0° with rapid stirring and the pH adjusted to 8.1 with 3.2µl 1.0N NaOH. The resulting solution was first saturated with argon and then reduced by adding 5µl 0.04M dithioerythritol-0.001M EDTA and subsequently storing it overnight under argon at 0° to give a thiolated G-6-PDH solution (14 $HS^{14}CH_2CO$-residues).

D. A solution of 19mg (0.2 mmole) of chloroacetic acid and 23mg (0.2mmole) of N-hydroxy succinimide was prepared in 1ml of dry dimethylformamide in a dried, nitrogen-purged flask. Dicyclohexylcarbodiimide (42mg, 0.2mmole) was added and the reaction was allowed to stir for 30 minutes. The entire reaction mixture was then added to a stirring suspension of thyroxine (154mg, 0.2mmole) in 5ml of DMF. The thyroxine dissolved within 1 hour. The reaction mixture was filtered through celite and was poured into 20ml of water. The heavy white precipitate which formed was isolated by filtration and dried to yield 160mg. Crystallization from ethyl acetate/pet. ether gave a small amount of material, mostly impurities by TLC. The product was collected by evaporating the mother liquor.

E. N-[1-$^{14}$C]-chloroacetamidothyroxine (2.3mg, 2.7µmoles) dissolved in 30µl of carbitol was added in portions (1µl/5sec.) with rapid stirring to thiolated G-6-PDH (fourteen $HS^{14}CH_2CO$-residues; 0.95mg) in 1.25ml solution containing 20% carbitol, 0.04M sodium phosphate, 3.2 × $10^{-4}$M dithioerythritol, 1.0 × $10^{-5}$M EDTA at 0°. Pooled fractions containing enzyme conjugate were concentrated to 1.0ml in a dialysis sack by applying dry Sephadex G-200 to the outside. Next it was rechromatographed on a fresh G-25 Sephadex column. Again pooled fractions containing enzyme conjugate were concentrated to 1.0ml with Sephadex G-200. Analysis indicated that four thyroxine residues were covalently incorporated in the enzyme conjugate.

EXAMPLE XVI

Conjugation of N,N-Dimethyl O-Carboxymethyl T-4 with m-MDH

A. To a mixture of methyl thyroxinate hydrochloride (1.66g, 2mmoles), formaldehyde (0.6ml, 37% in solution) and methanol (40ml, dried over molecular sieves 3A) was added, under nitrogen atmosphere, at room temperature, a solution of sodium cyanoborohydride (420mg) in 10ml of dry methanol. The reaction mixture was then stirred overnight at room temperature and the resulting product stripped to dryness. The residue was triturated with 20ml of chloroform, the solution concentrated, and then placed on a column (0.5 × 7in, silica gel, eluted with 500ml chloroform). Evaporation of eluents gave 1.52g (93% yield) of methyl N,N-dimethyl thyroxinate.

B. To N,N-dimethyl thyroxinate (306mg, 0.37mmole) in hexamethylphosphortriamide (dried on molecular sieves 3A, 5ml) was added under nitrogen at room temperature sodium hydride (50% in oil, 36mg, 0.75mmole), followed by sodium chloroacetate (405mg) and potassium iodide (547mg). The resulting mixture was stirred at 70°. After 18 hrs, an aliquot of the reaction mixture was dissolved in 1:1/MeOH:0.05N NaOH, and its UV spectrum taken. The disappearance of UV absorbance at 326mµ indicated completion of the reaction. The reaction product was then added to 40ml of ice-water containing 1ml of 10% HCl. The resulting white precipitate was collected and dried in vacuo. The product weighted 367mg ($R_f$ 0.42, silica gel plate 0.5:10:90/HOAc:MeOH:CHCl$_3$).

C. N,N-Dimethyl O-carboxymethyl T-4 (9.7 × $10^{-3}$g, 1.1 × $10^{-5}$mole), 1.2 × $10^{-3}$g (1.0 × $10^{-3}$mole) of NHS, and 250µl of dry DMF were added successively to a 1ml reaction vessel. The reaction mixture was cooled to ice bath temperature under a N$_2$ blanket. ECDI (2.1 × $10^{-3}$g, 1.1 × $10^{-5}$mole) was added to the reaction mixture, which was stirred overnight at 4°.

With cooling in an ice bath and with stirring, 0.45ml of DMF was added slowly to 4.2 × $10^{-3}$g (6.3 × $10^{-8}$mole) of m-MDH in 1.5ml of aq. 0.05M NaHCO$_3$.—Na$_2$CO$_3$(pH 9.0) buffer. The 4.4 × $10^{-2}$M T$_4$ phenolic acid N-hydroxysuccinimide ester solution was diluted 1 to 5, by addition of 1.0ml of ice cold DMF to give a 8.8 × $10^{-3}$M activated ester solution. 63µl of the 8.8 × $10^{-3}$M T$_4$ phenolic acid N-hydroxysuccinimide ester solution was added slowly to the conjugation mixture containing the m-MDH. 0.27ml of 0.05M NaHCO$_3$—Na$_2$CO$_3$(pH 9.0) buffer was then added to the conjugation mixture, followed by 120µl more of the 8.8 × $10^{-3}$M activated ester. The conjugation mixture was allowed to stir for one-half hour at ice bath temperature, then was gel filtered on three 0.9 × 55cm Sephadex G-50M columns to yield a T$_4$-phenolic acid/m-MDH conjugate which was 84% deactivated and which had a hapten number of 7.0 (by iodine analysis). The conjugate was found to be 21% inhibited by anti-(T$_4$phenolic imidate-BSA) and 11% activated by other anti T$_4$-sera.

EXAMPLE XVII

Conjugation of Thyroxine Galacturonamide to BSA

A.1 A suspension of methyl thyroxinate, 300mg (0.363mmoles), in ~ 15ml of dry dichloromethane containing 200mg of galacturonic acid diacetonide and 100µl triethylamine was cooled in an ice bath. A solution of ECDI in about 5ml dichloromethane was added over a 3 hour period. The mixture was allowed to warm to room temperature overnight.

The reaction mixture was filtered and concentrated at reduced pressure to yield an oil. This was chromatographed on 20g of Silica Gel PF eluted with CH$_2$Cl$_2$—THF-acetone (96:2:2) to afford 286mg (69%) of the galacturonamide as a glassy solid. Attempts to crystallize this material were unsuccessful.

A.2 Galacturonic acid diacetonide (55.2mg, 2mmole) was dissolved in 1ml tetrahydrofuran (freshly distilled from lithium aluminum hydride) with 28µl of triethylamine (0.2mmole) in a dried, nitrogen-purged round-bottomed flask fitted with a rubber septum. The solution was cooled to −30° and 26.2ml of isobutyl chloroformate (0.2mmole) was added. A precipitate immediately formed. The reaction was allowed to stir under nitrogen at −30° for 15 minutes, and then was added (by syringe) to a suspension of 165mg thyroxine methyl ester hydrochloride (0.2mmole) in 5ml tetrahydrofuran (distilled) and 28µl triethylamine (0.2mmole stirring under nitrogen at 0° whereupon analytical thin-layer-chromatography (silica gel; 96% dichloromethane, 2% each of tetrahydrofuran and acetone) showed virtually complete depletion of starting material. The reaction mixture was filtered through a Celite pad, reduced to 1ml volume on the rotovap, and purified by preparative thin-layer chromatography on one 40cm by 20cm by 1mm silica gel plate using the above-described developing solvent. The appropriate band ($R_f$ about 0.7) was removed and eluted with tetrahydrofuran which was evaporated in vacuo to yield 150mg pale yellow foam; 80% of theoretical yield.

B. A mixture of 286mg methyl thyroxinate galacturonamide diacetonide and 1.5ml glacial acetic acid, 1ml water, and 1ml 1N HCl was heated to reflux until the mixture became homogeneous (~2hr). An additional 1ml of HCl was added and the heating continued until TLC indicated the absence of starting material. The flask was allowed to cool overnight. The product solidified into a brown crystalline mass. Recrystallization twice in hot aqueous methanol (decolorizing carbon) afforded a nearly white microcrystalline powder as the hydrate, 137mg (52%).

C.1 To a solution of 100mg (0.09 meq lysines) bovine serum alumin and 50mg (0.05mmoles) thyroxine galacturonamide in 10ml 0.05M pH 7 phosphate buffer and 2ml dimethylformamide was added 20mg (0.32mmoles) sodium cyanoborohydride in one portion. After six days at room temperature the solution was centrifuged at 12,500rpm for 10min. The supernatant was concentrated to 3-4ml in a Mini-dialyzer. The concentrate was chromatographed on ~ 10g silica gel G-100 eluted with 0.1M Trisphosphate, pH 9.1. Two overlapping fractions were collected. These were dialyzed with 6l. of water in three portions. During the dialysis the protein began to precipitate. The uv spectra of these fractions were identical. They were redissolved with a little aqueous ammonium carbonate, combined and lyophilized to afford 82mg of conjugate with a hapten number of about 6.

C.2 Thyroxine-galacturonamide (84mg, .086mmole) in 8ml 0.05N aqueous sodium hydroxide was acidified to pH 11 with dilute aqueous hydrochloric acid. Solid cyanogen bromide 10.1mg (0.095mmole) was added all at once. The pH began dropping immediately and was maintained at pH 11 by the addition of 1N aqueous sodium hydroxide; the temperature was kept near 25° by periodic cooling of the reaction vessel in an ice bath. The pH drop slowed after about 10 minutes and the reaction mixture was immediately added to a solution of 113mg bovine serum albumin (Pentex, about 0.1mmole of lysine) in 8ml of 0.1M carbonate buffer, pH 9.2, cooled to 0°-4° for 4 hours. The reaction mixture was then place in a dialysis bag (Spectra por, 6,000-8,000 molecular weight cutoff) and dialyzed against 20 l. of 2% sodium bicarbonate solution in the rocking tube dialyzer over a period of 15 hours, and then against 20 l. of deionized water over another 15 hour period. The hapten number was calculated from the ultraviolet absorption spectrum of the conjugate (water, pH 12) to be about 12.5 haptens per BSA molecule.

EXAMPLE XVIII

Conjugation of $T_4$-galaturonamide to m-MDH

To a 1.8ml ice cold solution of m-MDH (1.9mg/ml) in 0.03M $NaHCO_3$—$KH_2PO_4$ (pH 6.9) was added dropwise 350$\mu$l of 2.8 × $10^{-3}$M $T_4$-galacturonamide in DMF solution, followed by sufficient 1.0N HCl to adjust the pH to 6.9. After stirring for 15 minutes at ice bath temperature, 45$\mu$l of the 2.5 × $10^{-2}$M sodium cyanoborohydride in 1:2 DMF $H_2O$ solution was added dropwise. The reaction mixture was stirred for 7 days at 4°. The reaction mixture was then dialyzed for two days against 0.05M $Na_2HCO_3$—$Na_2CO_3$ (pH 9.0) buffer (2 × 100ml) then dialyzed further against 100ml of 1.0ml of 1.0M $K_2HPO_4$ + 1mM $NaN_3$ for 1 day. The dialyses were conducted at 4°. The conjugate was found to have a hapten number of 5.4 and was 44% deactivated. The enzyme activity of the conjugate was unaffected upon treatment with various anti-$T_4$ sera.

EXAMPLE XIX

Preparation of T-4 hemisuccinamide-BSA conjugate

A. Methyl thyroxinate hydrochloride 1.65gm, 0.002m was suspended in 150ml dry THF contained in a 250ml flask protected from light. Triethylamine (300$\mu$l, 0.0021m) was injected into the stirring suspension followed by the addition of 200mg (0.0022m) succinic anhydride. The reaction mixture was stirred overnight. When analytical TLC showed that the reaction was complete (20% MeOH/$CHCl_3$) the solution was washed 3x with 10% NaCl, dried with $Na_2SO_4$, and the solvent evaporated. The residue was purified on a 30gm Sephadex LH-20 column using 20% methanol in acetone as eluent. The clean fractions were collected and the solvent removed. Precipitation was accomplished from methanol with water. Obtained 1.65gm of the amide, yield 92%.

B. Dioxane (10ml) was added to a solution of 100mg BSA (~.1mmole lysines) in 20ml 6M guanidine hydrochloride. A 6ml solution of 222mg $T_4$-hemisuccinamide (.25mmole) in dioxane was added dropwise to the protein solution at room temperature. The mixture was then cooled to 0° and to it was added every 15 minutes 1ml of a 4ml water solution of 60mg (0.3mmole) ECDI. A few minutes after the addition of the ECDI, a precipitate appeared and increased as the reaction continued stirring overnight in the cold room. The precipitate was spun down and the supernatant dialyzed in a Dow Beaker Ultrafilter against 10gal of 0.05M carbonate, pH 9 buffer, then against 5gal deionized water. Lyophilization afforded 86mg of a $T_4$-hemisuccinamide-BSA conjugate with a hapten number of 13.5 (U.V.).

Antibodies were prepared employing the antigen conjugate of Example II. Initially 2mg of the conjugate was injected. Then 0.25mg of the conjugate was injected at two week intervals. With sheep, the individual injection was a total of 2ml, of which 0.5ml was the conjugate dissolved in saline plus 1.5ml of Freund's complete adjuvant. Aliquots (0.25ml) were injected subcutaneously into each of 4 sites and 0.5ml aliquots were injected intramuscularly into each hind leg.

With rabbits, the total injection was 0.75ml, with 0.25mg of the conjugate dissolved in 0.25ml saline, and 0.5ml of Freund's complete adjuvant added. Injections of 0.09ml were injected subcutaneously into 4 sites and injections of 0.19ml injected into each hind leg.

The animals are normally bled about 5 to 7 days after each injection and the antibodies isolated according to conventional procedures.

To demonstrate the utility of the thyroxine-MDH conjugate for assaying for $T_4$, a number of assays were carried out. In a first series of assays, the assays were carried out with varying amounts of antibody to demonstrate the increase in activity of the enzyme conjugate with increasing amounts of antibody. In a second series of assays, varying amounts of $T_4$ were added to antibody, so as to change the effective concentration of antibody which is available for binding to the MDH-bound-thyroxine. From these results it is shown, that by establishing a standard curve based on samples containing known amounts of thyroxine, one can determine the amount of thyroxine which is in serum by relating the observed values of the enzyme activity to the standard curve.

The assay procedure is as follows. To 0.8ml of 0.1 weight percent RSA in 0.1M glycinate buffer, pH 9.5, containing $10^{-3}$M EDTA, is added the antibody solution, followed by the addition of MDH-bound-T-4. The solution is incubated for 45 minutes, at which time the substrates (100$\mu$l 2M malate and 100$\mu$l 0.108M NAD) are added and the solution is transferred to a spectrophotometer and the values read at 30°, as the change in optical density between 120 seconds and 60 seconds from the introduction into the spectrophotometer. For the conjugates prepared in Example III, employing sheep antibody, the following table indicates the results.

TABLE II

| | Conjugate Example III | | | |
|---|---|---|---|---|
| $Ab_{T-4}$[1] $\mu$l | $c^2$ % change | $d^2$ % change | $e^2$ % change | $f^2$ % change |
| 0 | — | — | — | — |
| 1 | +17 | 113 | 246 | 34 |
| 2 | +17 | 124 | 358 | 111 |
| 3 | +17 | 130 | 389 | 190 |
| 4 | +17 | 126 | 399 | 290 |
| 5 | +17 | 129 | 427 | 376 |
| 10 | +17 | 130 | 467 | 665 |
| 15 | +17 | 136 | 471 | 725 |
| 20 | +17 | 139 | 503 | 829 |
| 25 | +17 | 144 | 485 | 825 |

[1] ~9.0 × $10^{-6}$ M $Ab_{T-4}$ based on binding sites; K = 1.12 × $10^9$
[2] Concentration (M) of enzyme conjugate TABLE II-continued

| $Ab_{T-4}^1$ μl | Conjugate Example III | | | |
|---|---|---|---|---|
| | $c^2$ % change | $d^2$ % change | $e^2$ % change | $f^2$ % change |
| sites per liter | | | | |
| c - 5 × $10^{-10}$ | | e - 1.4 × $10^{-8}$ | | |
| d - 2.56 × $10^{-9}$ | | f - 3.7 × $10^{-8}$ | | |

A series of assays were now carried out, whereby a thyroxine solution of 9.7mg in 25ml of 0.05N sodium hydroxide was serially diluted with 0.05N sodium hydroxide. The assays were carried out by combining 600μl of 0.1% rabbit serum albumin, 100μl of antibody in 0.1M glycine buffer, pH 9.5, $10^{-3}$M EDTA and 100μl of $T_4$ solution and the mixture incubated for 15 minutes at room temperature. To the solution was then added a specified volume of the MDH-bound-T-4 solution and the mixture incubated for 10 minutes. The substrates were then added and readings were taken in a spectrophotometer at 30° as indicated previously. The following table indicates the results.

TABLE III[3]

| $T_4$ Sample conc, M | Conjugate[1,2] | | |
|---|---|---|---|
| | c ΔOD | d ΔOD | e ΔOD |
| — | 91 | 81 | 248 |
| 5 × $10^{-10}$ | 89 | 83 | 254 |
| 5 × $10^{-9}$ | 88 | 82 | 255 |
| 5 × $10^{-8}$ | 90 | 81 | 249 |
| 5 × $10^{-7}$ | 88 | 77 | 212 |
| 5 × $10^{-6}$ | 95 | 54 | 93 |
| 5 × $10^{-5}$ | 99 | 56 | 85 |

[1]volume of enzyme conjugate employed and concentration
c - 15μl 1.11 × $10^{-7}$M
d - 5μl 5.12 × $10^{-7}$M
e - 5μl 2.81 × $10^{-6}$M
[2]anti-thyroxine 9 × $10^{-6}$M in binding sites diluted 1 to 33 prior to addition as 100μl
[3]ΔOD × $10^3$ Employing the G-6-PDH conjugate, the following assays were carried out. The $T_4$-G-6-PDH conjugate was incubated for about 1 hour at room temperature with antisera for $T_4$ derived from rabbits. Sheep anti-rabbit gamma-globulin (Antibodies Inc., Davis Calif. or Alpha Gamma Labs, Sierra Madre Calif.) was added and the mixture incubated for 20 to 30 minutes at room temperature. The suspensions were centrifuged and aliquots of the supernatants were diluted and assayed for enzymatic activity. The assay medium is 49mM tris (pH 7.8), 0.9mM sodium azide, 4.6mM NAD and 11.6mM G-6-P with a final volume of 0.9ml. 0.10ml of the supernatant was employed. Either 0.9 weight percent BSA or 0.09 weight percent RSA are included in the assay medium to prevent sticking of the conjugate to the container. The activity is determined at 37° C by following the change in absorbance at 340nm in a Gilford model 300-N spectrophotometer equipped with a thermocuvette. The concentration of antisera as based on binding sites was: for anti-(T-4-Memida-BSA), $\sim 10^{-7}$M; anti-(T-4 hemisuccinamide-BSA), 5 × $10^{-7}$M. Comparison runs were carried out with native G-6-PDH to determined whether the procedure would affect unconjugated G-6-PDH. The following table indicates the results for the 2 different conjugates.

TABLE IV

| Antisera | Conj. | % Change in Activity of Supernatant | |
|---|---|---|---|
| | | Native G-6-PDH | Conjugate |
| Anti-$T_4$-Memida BSA | 1 | −6.4 | −18.2 |
| Anti-T-4-Hemisuccinamide-BSA+ anti-IgG* | 2 | +4.4 | −21.3 |

*Alpha Gamma Labs, Gamma Gel, 6 × $10^{-7}$M insolublized

It is evident from the prior results, the conjugates can be obtained between $T_4$ and a wide variety of enzymes, whereby the enzymes undergo substantial changes in activity to be useful in enzyme immunoassays. The conjugates can be used for both homogeneous enzyme immunoassays, where no separation is required, and heterogeneous enzyme immunoassays, where separation is required. The enzymes are found to have significant shelf life. Depending upon the particular enzyme, deactivation or activation of the enzyme can be observed when the conjugated enzyme is bound to antibody.

Although the foregoing invention has been described in some detail by way of illustration and example for purposes of clarity of understanding, it will be obvious that certain changes and modifications may be practiced within the scope of the appended claims.

What is claimed is:

1. A thyroxine conjugate to an enzyme at other than the active site of the enzyme, having on the average from about 1 to 20 of said thyroxines bonded to said enzyme, wherein said thyroxine conjugated enzyme undergoes a substantial change in the enzymatic activity of said enzyme upon binding of receptor for said thyroxine to the thyroxine conjugated to said enzyme.

2. A thyroxine enzyme conjugate of the formula

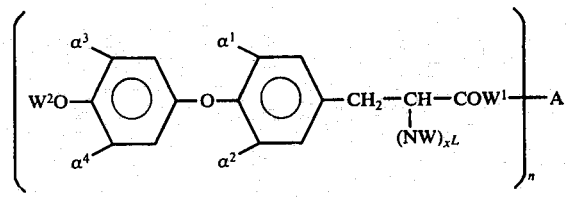

wherein:
any one of the W groups can be X or an H of any one of the W groups may be replaced by X, wherein X is a bond or linking group;
X is 0 or 1, being 0 when $W^1$ is the linking group;
A is an enzyme bonded at other than its active site;
n is on the average in the range of 1 to the molecular weight by A divided by 2,000;
$a^{1-4}$are iodine;
L is hydrogen or when $W^2$ is ehe linking group, lower alkyl of from 1 to 3 carbon atoms or a protective acyl group;
when other than a linking group:
W and $W^2$ are hydrogen, with the proviso that when L is lower alkyl, W is lower alkyl of from 1 to 3 carbon atoms; and
$W^1$ is hydroxyl or lower alkoxyl of from 1 to 3 carbon atoms.

3. A polyiodothyronine conjugate according to claim 2, wherein W is the linking group and A is an oxioreductase.

4. A polyiodothyronine enzyme conjugate according to claim 2, wherein W is the linking group and A is a hydrolase.

5. A polyiodothyronine enzyme conjugate according to claim 2, wherein W is the linking group and A is an isomerase.

6. A polyiodothyronine enzyme conjugate according to claim 2, wherein $W^2$ is the linking group and A is an oxidoreductase.

7. A polyiodothyronine enzyme conjugate according to the formula

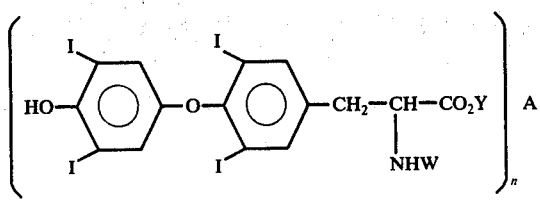

wherein:
- Y is hydrogen or lower alkyl of from 1 to 3 carbon atoms;
- n is on the average in the range of 1 to 20;
- A is an enzyme bonded at other than the active site to the polyiodothyronine group in the parenthesis;
- W is a linking group which is a bond or aliphatic group of from 1 to 16 atoms other than hydrogen, which are carbon, oxygen, nitrogen, or sulphur, the oxygen and sulphur being present as oxy or oxo or thioanalogs thereof and the nitrogen being present as amido or tertiary amino.

8. A polyiodothyronine enzyme according to claim 7, wherein n is in the range of 2 to 12 and A is an oxidoreductase.

9. A polyiodothyronine enzyme conjugate according to claim 7, wherein m is in the range of 2 to 12 and A is an hydrolase.

10. A polyiodothyronine enzyme conjugate according to claim 7, wherein W is of the formula

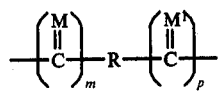

wherein:
- M and $M^1$ are chalcogen or nitrogen;
- m and p are either 0 or 1, the sum of m plus p being in the range of 0 to 2;
- R is a bond or an aliphatic group of from 1 to 8 carbon atoms and includes from 0 to 1 heteroatom of atomic number 7 to 8, oxygen being present as oxy or oxo and nitrogen being present as tertiary amino or amido.

11. A thyroxine conjugate to an enzyme at other than the active site of the enzyme, having on the average from about 1 to 20 of said thyroxine bonded to said enzyme.

12. A thyroxine conjugate to glucose-6-phosphate dehydrogenase having from 1 to 12 thyroxine groups bonded to said glucose-6-phosphate dehydrogenase by amide linkages or the nitrogen or thio analog thereof.

13. A thyroxine conjugate according to claim 12, wherein said thyroxine is bonded through the thyroxine amino by a diglycoldioyl group.

14. A thyroxine conjugate to glucose oxidase having from 1 to 12 thyroxine groups bonded to said glucose oxidase by amido linkages or the nitrogen or thio analogs thereof.

15. A thyroxine conjugate to lysozyme having from 1 to 5 thyroxine groups bonded to said lysozyme by amide linkages or the nitrogen or thio analogs thereof.

16. A desaminothyrozine conjugate to glucose-6-dehydrogenase having from 1 to 12 desaminothyroxine groups bonded to said glucose-6-phosphate dehydrogenase by amide linkages or the nitrogen or thio analog thereof.

* * * * *